United States Patent [19]
Vinciguerra et al.

[11] Patent Number: 5,554,158
[45] Date of Patent: Sep. 10, 1996

[54] INTERCONDYLAR NOTCH CUTTER FOR POSTERIOR STABILIZED FEMORAL KNEE PROSTHESIS

[75] Inventors: John D. Vinciguerra, Austin; Charles H. Perrone, Jr., Georgetown; Charles W. Mumme; Jeffery C. Higgins, both of Austin, all of Tex.

[73] Assignee: Intermedics Orthopedics, Inc., Austin, Tex.

[21] Appl. No.: 451,530

[22] Filed: May 26, 1995

Related U.S. Application Data

[63] Continuation of Ser. No. 252,689, Jun. 2, 1994, abandoned.

[51] Int. Cl.⁶ ............................................... A61B 17/56
[52] U.S. Cl. ............................ 606/80; 606/88; 623/20
[58] Field of Search .................... 606/88, 87, 89, 606/86, 96, 99, 79, 80, 81, 53, 167, 180; 623/20, 18, 16

[56] References Cited

U.S. PATENT DOCUMENTS

| | | | |
|---|---|---|---|
| 4,213,209 | 7/1980 | Insall . | |
| 4,298,992 | 11/1981 | Burstein . | |
| 4,470,158 | 9/1984 | Pappas | 623/20 |
| 4,721,104 | 1/1988 | Kaufman | 606/88 |
| 4,896,663 | 1/1990 | Vandewalls | 606/79 |
| 5,007,933 | 4/1991 | Sidebotham et al. | 623/20 |
| 5,035,699 | 7/1991 | Coates | 606/86 |
| 5,098,436 | 3/1992 | Ferrante | 606/88 |
| 5,100,409 | 3/1992 | Coates | 606/88 |
| 5,176,684 | 1/1993 | Ferrante | 606/88 |
| 5,192,293 | 3/1993 | Cartwright et al. | 606/172 |
| 5,258,032 | 11/1993 | Bertin | 623/20 |
| 5,324,295 | 6/1994 | Shapiro | 606/86 |

*Primary Examiner*—Guy Tucker
*Attorney, Agent, or Firm*—Richard L. Robinson

[57] ABSTRACT

An intercondylar notch cutter using a plunge milling bit and bit guide which engages parallel tracks in a trial prosthesis. The intercondylar notch cutter comprises a cutting bit and a guide sleeve. The cutting bit can be thrust into the femur and then translated through the femur cutting a notch without removing the trial prosthesis. The bit is supported by a guide or housing with a guide platform which extends medially and laterally from the guide. Two condyle articulating surfaces on the platform slidingly engage a condyle surface on a trial prosthesis. Along the condyle surfaces on the trial prosthesis are two parallel grooves. Posts on the notch cutter are slidingly received within the grooves. A surgeon first places the trial implant on the femur without cutting an intercondylar notch. The surgeon can proceed immediately to cut an intercondyle notch without removing the femoral trial prosthesis.

8 Claims, 2 Drawing Sheets

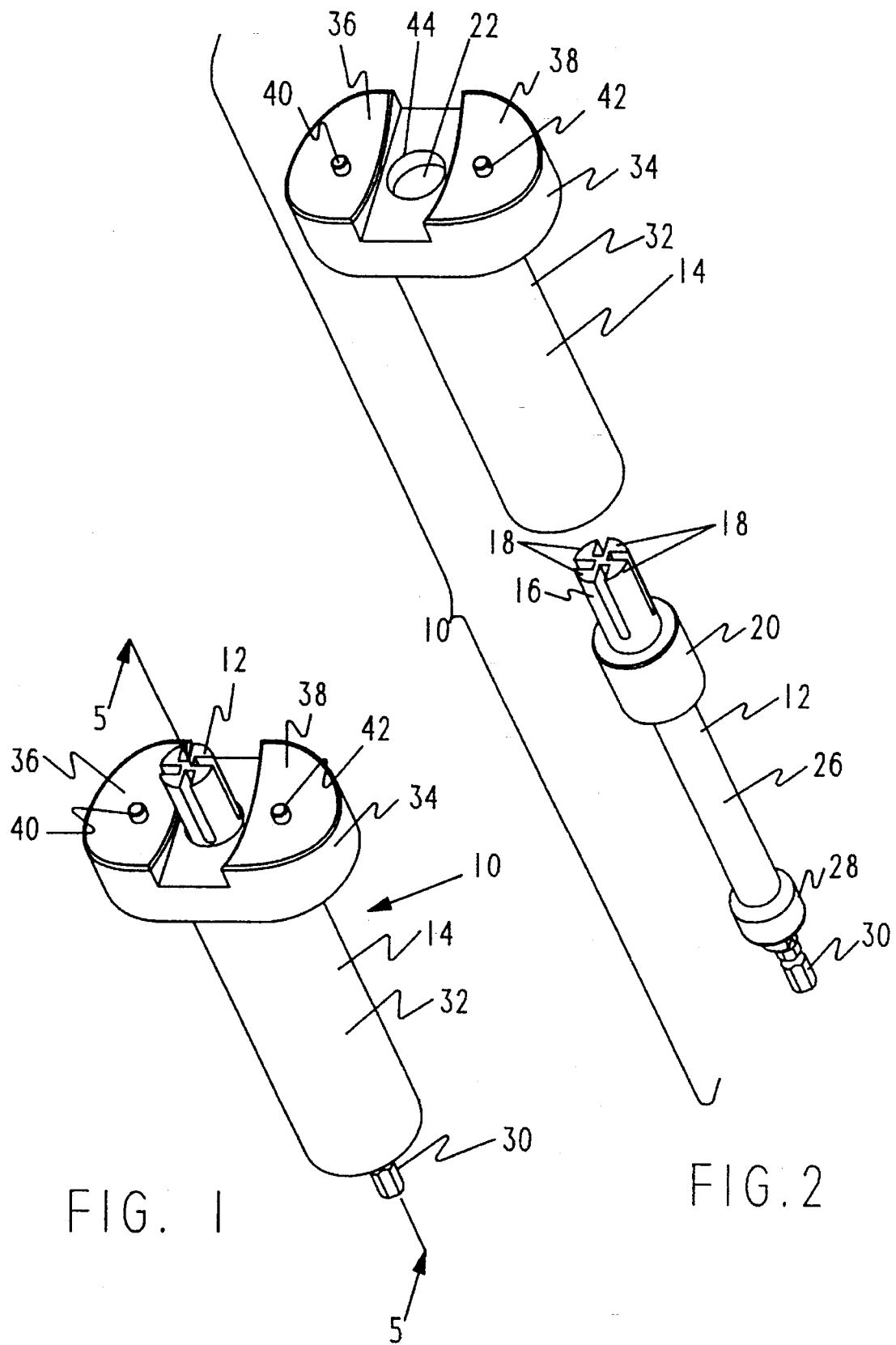

5,554,158

INTERCONDYLAR NOTCH CUTTER FOR POSTERIOR STABILIZED FEMORAL KNEE PROSTHESIS

This is a continuation of application Ser. No. 08/252,689 filed on Jun. 2, 1994, now abandoned.

FIELD OF THE INVENTION

This invention relates generally to orthopedic surgical devices and in particular to instrumentation used to prepare the distal surface of a femoral bone to receive a posterior stabilized knee prosthesis.

BACKGROUND OF THE INVENTION

Many kinds of prosthetic implantable knee prostheses are known to those skilled in this art. One type of knee prosthesis is a posterior stabilized prosthesis, such as those shown in U.S. Pat. Nos. 4,213,209 and 4,298,992. In the posterior-stabilized prosthesis, the tibial component has a central keel or post which extends upwardly from an articulating surface, and is adapted to extend between the condyles of the mating femoral prosthesis. This keel may be captured in a box structure or there may be a transverse post or bar which extends between the posterior portions of the condyles of the femoral prosthesis. As the knee articulates the keel engages sides of the femoral prosthesis located adjacent the condyles, thereby stabilizing the action of the knee. As the knee approaches full flexation, the keel commonly encounters a back wall of the box or the aforementioned transverse bar. The interaction of the keel and bar operate to force the femoral component to roll slightly posteriorly along the tibial component.

In order to employ such a prosthesis, it is necessary to cut away a portion of the femur which will lie between the condyles of the femoral prosthesis. Such a removal of bone material is necessary so that the keel may slide between the condyles without obstruction. Various jigs and apparatus have been proposed for the removal of the bone material between the condyles. An example is U.S. Pat. No. 5,176,684 to Ferrante, et al. and related U.S. Pat. Nos. 5,100,409 to Coates, et al. and 5,098,436 to Ferrante, et al.

SUMMARY OF THE INVENTION

We have invented an intercondylar notch cutter using a plunge milling bit and a bit guide which engages parallel tracks in a posterior stabilized femoral trial prosthesis. The intercondylar notch cutter comprises a cutting bit and a guide sleeve. The cutting bit can be thrust into the femur and then translated through the femur cutting a notch. A bit is supported by a guide or housing which comprises a hollow cylindrical shaft and a guide platform which extends medially and laterally from the cylinder. Two condyle articulating surfaces are provided on the platform. These surfaces slidingly engage a condyle surface on a trial prosthesis. Along the condyle surfaces on the trial prosthesis are two parallel grooves. Posts on the notch cutter are slidingly received within the grooves. A surgeon will be able to place the posterior stabilized femoral trial on the femur without first cutting an intercondylar notch. The anterior-posterior motion of the notch cutter is limited by the length of the parallel grooves. Thus, a minimum amount of bone is removed, allowing clearance for a keel of an articulating surface of a posterior stabilized tibial prosthesis, but conserving as much bone as possible.

It is a principle object of the invention to provide an intercondyle notch cutter which utilizes the trial femoral prosthesis.

Another object of the invention is to provide a notch cutter which can be used after a femoral trial prosthesis has been implanted and without removing the trial prosthesis.

It is a further object of the invention to provide a notch cutter which removes a minimal amount of bone.

Yet another object of the invention is to provide a notch cutter which is limited in anterior-posterior motion.

A further object is to provide a notch cutter having a cutting implement which is limited to following a proposed path for a keel of a posterior stabilized tibial component.

These and other objects and features of the invention will be apparent from the following detailed description, taken with respect to the accompanying drawings.

BRIEF DESCRIPTION OF THE DRAWINGS

FIG. 1 is a perspective view of an intercondylar notch cutter according to the invention.

FIG. 2 is an exploded perspective view of the notch cutter of FIG. 1.

DETAILED DESCRIPTION OF THE INVENTION

The invention is described below with reference to the accompanying drawings.

Figure 5:
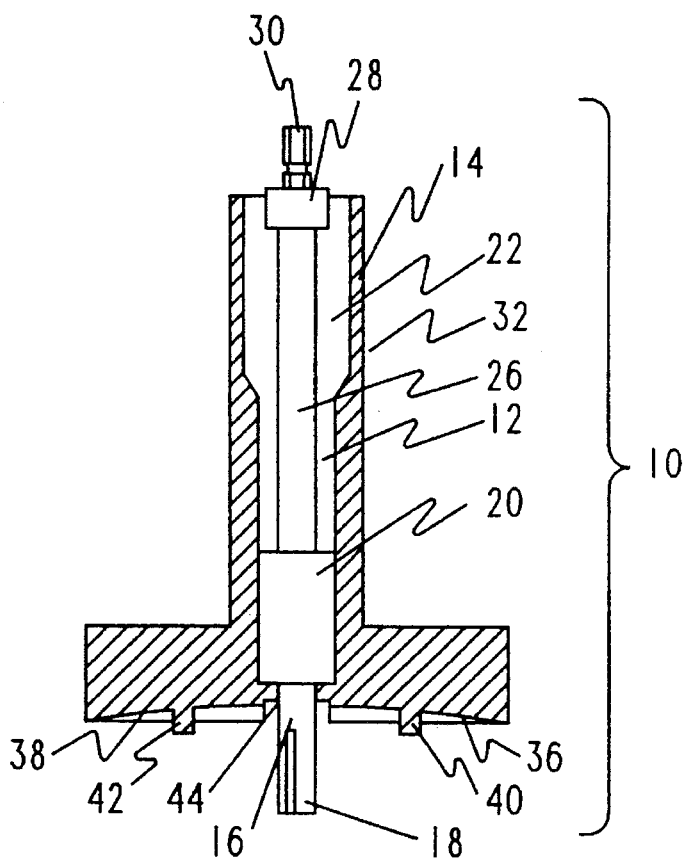
FIG. 5 is a cross sectional view of the intercondylar notch cutter of FIG. 1, take along line 5—5 of FIG. 1.

Referring to FIGS. 1, 2, and 5, the intercondylar notch cutter 10 comprises a cutting bit 12 and a guide sleeve or bushing 14. The cutting bit 12 has a milling head 16 at a distal end thereof. The milling bit 16 comprises four cutting blades 18 which allow the bit to be thrust into the femur and then translated through the femur, cutting a notch. Proximal from the blades 18 there is a bushing surface 20 which engages an inner surface of a cylindrical bore 22 in the guide 14. Proximal from the bushing surface is a shaft 26 and a gripping surface 28. Proximal from the gripping surface 28 there is a drive connector 30 which is adapted to engage a source of rotary motion, such as is commonly available in an operating theater.

The bit 12 is supported by the guide sleeve 14 which comprises a hollow cylindrical shaft 32 which serves both as a handle for the apparatus and as support for the bit 12. Distally on the cylindrical shaft 32 there is a guide platform 34 which extends medially and laterally from the cylinder 32. Two condyle articulating surfaces 36, 38 are provided. These surfaces 36, 38 are configured to slidingly engage a condyle surface on a trial prosthesis, to be described below. Each articulating surface 36, 38 has a guide pin 40, 42 or guide rail which is adapted to engage slots in the femoral trial prosthesis. A through bore 44 fits the bit 12.

Figure 3:
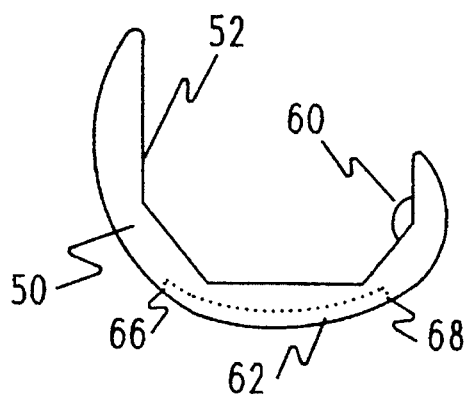
FIG. 3 is a side view of a femoral trial implant suitable for use with the notch cutter of FIG. 1.
Figure 4:
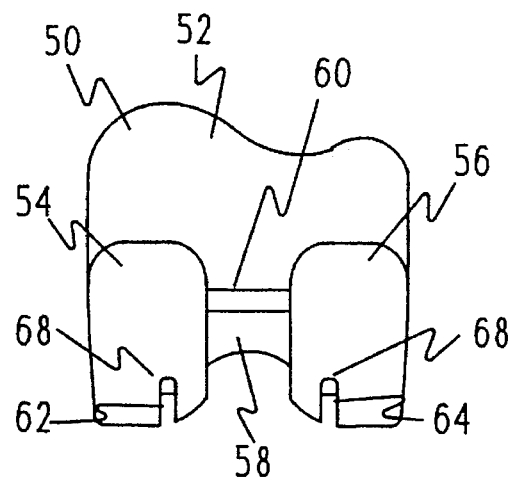
FIG. 4 is a front view of the femoral trial prosthesis of FIG. 3.

Referring to FIGS. 3 and 4, a complementary posterior stabilized femoral trial prosthesis 50 is shown. It is known in this art to resect the distal surface of a femur and to place a trial prosthesis thereon to check the geometry of the knee. The invention can be used with the trial prosthesis in position. Without removing the femoral trial prosthesis 50, the surgeon will be able to cut an intercondylar notch, replace the tibial articulating surface with a surface having a central keel or post and recheck the knee for proper functioning.

To this end, the femoral trial prosthesis 50 has an internal box geometry 52 which will mate with the resected distal surface of the femur. Two condyle articulating surfaces 54, 56 are provided. A bridge 58 connects these two surfaces. A permanent or removable posterior stabilizing bar 60 may also be provided. Along the condyle articulating surfaces are two parallel grooves 62, 64. The guide pins 40, 42 on the notch cutter 10 are adapted to be slidingly received within the grooves 62, 64. Ends of the grooves, such as ends 66, 68, act as stops to limit the anterior-posterior range of motion of the notch cutter. The stops allow the proper range of resection necessary to duplicate the path of the keel of the posterior stabilized tibial prosthesis.

Using the invention, the surgeon will be able to place the trial implant on the femur without first cutting an intercondylar notch. Then the surgeon can proceed immediately to cut the intercondylar notch without removing the femoral condyle trial prosthesis.

The invention may be embodied in other specific forms by those skilled in the art without departing from the spirit or essential teachings thereof. The foregoing description, therefore, is intended in all respects to be illustrative, and the invention is to be defined by the appended claims.

We claim:

1. A surgical apparatus for cutting an intercondylar notch in a distal end of a patient's femur for receiving a posterior stabilized knee prosthesis, said apparatus comprising:

a distal femoral trial prosthesis having an anterior side and a posterior side, a notch cutter, and means for guiding said notch cutter with respect to said trial prosthesis, said distal femoral trial prosthesis providing access to an area of the distal end of the patient's femur between the medial and lateral condyles and having at least one trial condylar articulating surface replicating a condylar articulating surface of a corresponding permanent femoral prosthesis, said notch cutter having means for slidingly stabilizing said notch cutter on said trial condylar articulating surface for relative sliding articulation, and means connected to said stabilizing means for milling a notch in said area between said medial and lateral condyles, said means for guiding including at least one slot and means for tracking said slot, and means for limiting the motion of said notch cutter in a direction from said posterior side to said anterior side, said at least one slot being in said trial prosthesis, and said means for limiting motion comprises end stops on said at least one slot.

2. A surgical apparatus for cutting an intercondylar notch in a distal end of a patient's femur for receiving a posterior stabilized knee prosthesis, said apparatus comprising:

a distal femoral trial prosthesis having an anterior side and a posterior side, a notch cutter, and means for guiding said notch cutter with respect to said trial prosthesis, said distal femoral trial prosthesis providing access to an area of the distal end of the patient's femur between the medial and lateral condyles and having at least one trial condylar articulating surface replicating a condylar articulating surface of a corresponding permanent femoral prosthesis, said notch cutter having means for slidingly stabilizing said notch cutter on said trial condylar articulating surface for relative sliding articulation, and means connected to said stabilizing means for milling a notch in said area between said medial and lateral condyles, said means for guiding including two parallel slots and means for tracking said slots, and means for limiting the motion of said notch cutter in a direction from said posterior side to said anterior side, said means for limiting motion comprising end stops on said slots.

3. A surgical apparatus for cutting an intercondylar notch in a distal end of a patient's femur for receiving a posterior stabilized knee prosthesis, said apparatus comprising:

a distal femoral trial prosthesis having an anterior side and a posterior side, a notch cutter, and means for guiding said notch cutter with respect to said trial prosthesis, said distal femoral trial prosthesis providing access to an area of the distal end of the patient's femur between the medial and lateral condyles and having at least one trial condylar articulating surface replicating a condylar articulating surface of a corresponding permanent femoral prosthesis, said notch cutter having means for slidingly stabilizing said notch cutter on said trial condylar articulating surface for relative sliding articulation, and means connected to said stabilizing means for milling a notch in said area between said medial and lateral condyles, said at least one trial condylar articulating surface comprising a medial articulating surface and a lateral articulating surface, said medial and lateral articulating surfaces being spaced apart from one another to provide said access to said area of the patient's femur between the medial and lateral condyles, said means for guiding comprising at least one slot and means for tracking said slot, and means for limiting the motion of said notch cutter comprising end stops on said at least one slot.

4. The surgical apparatus according to claim 3 wherein the at least one slot is in said trial prosthesis.

5. A surgical apparatus for cutting an intercondylar notch in a distal end of a patient's femur for receiving a posterior stabilized knee prosthesis, said apparatus comprising:

a distal femoral trial prosthesis having an anterior side and a posterior side, a notch cutter, and means for guiding said notch cutter with respect to said trial prosthesis, said distal femoral trial prosthesis providing access to an area of the distal end of the patient's femur between the medial and lateral condyles and having at least one trial condylar articulating surface replicating a condylar articulating surface of a corresponding permanent femoral prosthesis, said notch cutter having means for slidingly stabilizing said notch cutter on said trial condylar articulating surface for relative sliding articulation, and means connected to said stabilizing means for milling a notch in said area between said medial and lateral condyles, said at least one trial condylar articulating surface comprising a medial articulating surface and a lateral articulating surface, said medial and lateral articulating surfaces being spaced apart from one another to provide said access to said area of the patient's femur between the medial and lateral condyles, said means for guiding comprising two parallel slots and means for tracking said slots, said means for limiting the motion of said notch cutter comprising end stops on said slots.

6. The surgical apparatus according to claim 5 wherein said slots are in said trial prosthesis.

7. The surgical apparatus according to claim 6 wherein one of said slots is in said medial articulating surface and the other of said slots is in said lateral articulating surface and wherein said means for stabilizing comprises first guide means for sliding on said medial articulating surface and second guide means for sliding on said lateral articulating surface and said milling means is mounted between said first and second guide means, and said means for tracking said slots comprises a first pin on said first guide means and a second pin on said second guide means.

8. A surgical apparatus for cutting an intercondylar notch in a distal end of a patient's femur for receiving a posterior stabilized knee prosthesis, said apparatus comprising a distal femoral trial prosthesis having
    a medial condyle part adapted to fit onto a resected distal part of the femur in place of the patient's medial condyle, the medial condyle part having a first distal convex articulating surface with a first groove extending in an anterior-posterior direction along said first surface,
    a lateral condyle part adapted to fit onto the resected distal part of the femur in place of the patient's lateral condyle, the lateral condyle part having a second distal convex articulating surface with a second groove extending in an anterior-posterior direction along said second surface, parallel to said first groove,
    said medial and lateral condyle parts being spaced apart from each other a distance sufficient to allow cutting of said intercondylar notch therebetween, and an intercondylar notch cutter having
    a medial concave guide surface fitted to slide on said medial convex articulating surface, said medial guide surface having a first pin adapted to be slidingly received in said first groove,
    a lateral concave guide surface fitted to slide on said lateral convex articulating surface, said lateral guide surface having a second pin adapted to be slidingly received in said second groove,
    a sleeve mounted between said medial and lateral guide surfaces, and
    a milling bit rotatably received in said sleeve, said milling bit being adapted to fit between said medial and lateral condyle parts of said distal femoral trial prosthesis;

wherein each of said first and second grooves has end stops to limit motion of said intercondylar notch cutter in said anterior-posterior direction.

* * * * *